(12) United States Patent
Andréen et al.

(10) Patent No.: US 10,279,159 B2
(45) Date of Patent: May 7, 2019

(54) CATHETER COUPLING ARRANGEMENT

(71) Applicant: DENTSPLY IH AB, Molndal (SE)

(72) Inventors: Erik Andréen, Göteborg (SE); Fredrik Andersson, Göteborg (SE)

(73) Assignee: DENTSPLY IH AB, Mölndal (SE)

( * ) Notice: Subject to any disclaimer, the term of this patent is extended or adjusted under 35 U.S.C. 154(b) by 173 days.

(21) Appl. No.: 14/227,287

(22) Filed: Mar. 27, 2014

(65) Prior Publication Data

US 2016/0367793 A1 Dec. 22, 2016

(30) Foreign Application Priority Data

Mar. 28, 2013 (EP) ..................... 13161667

(51) Int. Cl.
*A61M 39/10* (2006.01)

(52) U.S. Cl.
CPC ...... *A61M 39/1011* (2013.01); *A61M 39/105* (2013.01); *A61M 2039/1027* (2013.01); *A61M 2039/1033* (2013.01); *A61M 2039/1044* (2013.01); *A61M 2039/1083* (2013.01); *A61M 2039/1088* (2013.01)

(58) Field of Classification Search
CPC ............ A61M 39/1011; A61M 39/105; A61M 2039/1088; A61M 2039/1083; A61M 2039/1033
See application file for complete search history.

(56) References Cited

U.S. PATENT DOCUMENTS 4,704,103 A * 11/1987 Stober .................. A61M 39/12
604/175
5,562,618 A * 10/1996 Cai ................... A61M 39/0208
604/175
(Continued)

FOREIGN PATENT DOCUMENTS

EP 0815977 A1 1/1998
EP 1556125 B1 8/2006
(Continued)

OTHER PUBLICATIONS

European Search Report, Application No. 13161667.4, Published Aug. 5, 2013.
(Continued)

*Primary Examiner* — Bradley J Osinski
(74) *Attorney, Agent, or Firm* — Perkins Coie LLP

(57) ABSTRACT

A coupling device for a tubular arrangement for medical use including a first connector part and a second connector part and, an engagement/disengagement member for at least assisting in engaging and disengaging the engagement between said connector parts, wherein the first connector part includes at least two female connecting portions arranged in a first connector surface and a guiding edge protruding from the first connector surface arranged around the at least two female connecting portions and the second connector part includes at least two male connecting portions arranged in a second connector surface, and wherein at least one of the first connector part and the second connector part includes a locking element arranged to rotatably engage with the engagement/disengagement member.

20 Claims, 4 Drawing Sheets

(56) References Cited

U.S. PATENT DOCUMENTS

| | | | | |
|---|---|---|---|---|
| 2003/0088213 A1* | 5/2003 | Schweikert | ....... | A61M 25/0097 604/177 |
| 2004/0034324 A1 | 2/2004 | Seese | | |
| 2005/0256461 A1* | 11/2005 | DiFiore | ............. | A61M 25/0075 604/247 |
| 2008/0287919 A1 | 11/2008 | Kimball | | |

FOREIGN PATENT DOCUMENTS

| | | |
|---|---|---|
| JP | 02-045759 | 3/1990 |
| JP | 2008-54927 | 3/2008 |
| WO | 2004037339 | 6/2004 |
| WO | 2006042016 A2 | 4/2006 |

OTHER PUBLICATIONS

Office Action for Japanese Patent Application No. 2016-504615, dated Dec. 5, 2017, with translation (9 pages).

* cited by examiner

CATHETER COUPLING ARRANGEMENT

RELATED APPLICATIONS

This patent application claims the benefit of and priority to EP Application Ser No. 13161667.4, filed on Mar. 28, 2013, which are herein incorporated by reference for all purposes.

TECHNICAL FIELD OF THE INVENTION

The present invention relates to a coupling device for a tubular arrangement for medical use, as well as a method for engaging the coupling device.

BACKGROUND OF THE INVENTION

Many medical devices incorporate elongate shafts such as tubes, which are intended for insertion into and through passageways of a living body such as tubs, stents and catheters intended for use in the urethral tract, the cardio-vascular system and the colon. A lot of these require coupling devices arranged for example for coupling of an element arranged to be inserted internally into the human body with tubes arranged externally of the human body. The most common type of this general grouping of tubular arrangements for medical use is catheters. Exemplary catheters include those intended for urological, angioplasty, valvuloplasty and anal irrigation uses, that is, adapted respectively for insertion into the urethra, the lumen of a blood vessel, heart passageway and the colon of a living body, normally a human body. Many of these tubular arrangements need to be connected and disconnected frequently, e.g. daily. Further, users of such coupling devices are not only healthcare specialists, but also often disabled persons or other persons in need of medical assistance, and which may frequently have reduced dexterity and the like. Many non-professionals have difficulty engaging most known coupling devices for tubular arrangements for medical use, as well as realize when and if the coupling device is engaged properly. An example of such a previously known coupling arrangement is disclosed in EP 1 556 125.

Furthermore, disabled persons, such as persons having a spinal cord injury or spina bifida or MS, with limited limb movement can often not perform their normal bowel functions without need for outside aids. Examples of such aids are drugs, digital stimulation, massage or colonic irrigation. Therefore, many users of a coupling device for tubular arrangements for medical use are disabled persons and persons with reduced fine motor skills. For this group of people engaging a coupling device in a proper way is a great and unwanted challenge. However, by being able to engage the coupling device themselves, it will bring the person receiving care a sense of freedom and independence.

Many tubular arrangements of this type comprise multiple lumens, such as two or more lumens. The coupling device then needs to have multiple connection portions, which need to be connected and engaged properly. Such connection devices for multi-lumen tubular arrangements thus provide even greater problems for the typical user.

Thus, a general problem for most known coupling devices for tubular arrangements for medical use is that they are difficult to engage for non-professionals and especially for disabled persons with impaired dexterity, due to the need of precision when engaging the coupling device. Engaging and disengaging a coupling device comprising male and female connection portions may be difficult for a non-disabled person, respectively extremely difficult for a disabled person.

Consequently, there is a need for an improved coupling device for tubular arrangement for medical use that is able to engage/lock more easily, and with reduced need for precision. There is also a need for a cost-efficient coupling device of this type. There is further a need for a coupling arrangement, which is easier to maintain in a clean condition. Still further, there is a need for a coupling arrangement, which provides clear and accurate feedback to the user when it is properly secured.

SUMMARY OF THE INVENTION

It is therefore an object of the present invention to at least partly overcome problems mentioned above, and to provide an improved coupling device for tubular arrangements for medical use with e.g. less need for precision when engaging the coupling device and that is easy to use.

One of the objects of the present invention is, therefore, to provide a coupling device of the kind defined in the introduction, and a method for engaging such a coupling device, by means of which the disadvantages referred to above are completely or at least partly removed.

This object is achieved in a coupling device and by means of a method for engaging the coupling device in the manner defined in the appended claims. These and other objects will be apparent in the following.

According to a first aspect of the invention there is provided a coupling device for a tubular arrangement for medical use comprising a first connector part and a second connector part, wherein one of said connector parts comprises an engagement/disengagement member for at least assisting in engaging and disengaging the engagement between said connector parts, and wherein the other of said connector parts comprises a locking element arranged to rotatably engage with the engagement/disengagement member, wherein the first connector part comprises at least two female connecting portions arranged in a first connector surface and wherein the second connector part comprises at least two corresponding male connecting portions arranged in a second connector surface, and wherein the first connector part further comprises a guiding edge protruding from the first connector surface towards the second connector part, and being arranged around said at least two female connecting portions.

The present invention is based on the insights that a coupling device for tubular arrangements for medical use, such as catheters, may be provided with a guiding element arranged to facilitate the engagement of the coupling device. It has been found that a guiding edge, an edge protruding from the first connector surface of the first connector part surrounding the at least two female connection portions, facilitates engagement of the coupling device, by forming a recess in the connection interface. The guiding edge, forming a recess together with the first connector surface in the first connector part, enables reduction of the need for precision when the engaging the coupling device, such that the at least two male connecting portions are brought between the guiding edge, instead of trying to directly by precision obtain the matching of the at least two male connecting portions with the at least two female connecting portions. Thus, the at least two male connecting portions may be brought with less precision to a substantially larger surface surrounded by the guiding edge, compared to engaging the smaller surface of the female connecting portions directly.

The guiding element may further restrict lateral movement of the second connector part, such that the at least two male connecting portions of the second connector part may be securely rotated along the first connector surface until they engage with the at least two female connecting portions in less than one turn of the second connector part. Further, the solution is relatively simple, enables a cost-efficient production and may be adapted for numerous tubular arrangements for medical use.

The coupling device may be locked by engaging the locking element arranged on at least one of the first and the second connector part with the engagement/disengagement member. The coupling device may be used in many medical devices incorporating elongate shafts and or probes such as tubes, which are intended, for insertion into and through passageways of a living body such as those of a urethral tract, cardiovascular system, colon and intestinal tract.

According to one example embodiment of the invention, the tubular arrangement is a catheter, and preferably, a catheter for anal irrigation, and at least one of the first and the second connector part is fixedly connected to said catheter.

The coupling device, i.e. one of the connector parts, may be fixedly connected to a catheter. Exemplary catheters include those intended for urological, angioplasty, valvuloplasty and anal irrigation uses, that is, adapted respectively for insertion into the urethra, the lumen of a blood vessel, heart passageway and the colon. In a preferred embodiment, the coupling device is fixedly connected to a catheter used for anal irrigation. A catheter for anal irrigation is typically provided with two passageways, one for the supply of irrigation liquid, and one for supplying a fluid to a balloon or other form of retention member, for inflation/expansion thereof. The inflatable balloon may be arranged in proximity to the distal end of the catheter. The catheter may be fixedly connected to either the first connector part or the second connector part.

According to one example embodiment of the invention, the guiding edge has a circular shape arranged to surround the at least two female connecting portions of the first connector part.

The guiding edge preferably has the shape of a circle, such that the at least two male connecting portions are guided by the guiding edge when the second connector part is rotated in a smooth and unobstructed manner. Thus, the guiding edge may keep the at least two male connecting portions in a position that will ensure engagement with the at least two female connecting portions when the second connector part is rotated. The guiding edge is further preferably arranged to narrowly surround the outer edges of the female connecting portions. The guiding edge may protrude from the surface of the first connector surface, creating a circumferential surface of for example a cylinder around at least part of the first connector surface comprising the at least two female connecting portions. The guiding edge may form a recess in the first connector part with the first connector surface. The shape of the recess may be a hollow cylinder. However, other shapes of the recess may also be conceivable such as cup-shaped, cone-shaped, or any other circular symmetric shape.

Similarly, the first connector surface is preferably essentially planar, and arranged essentially perpendicular to the axial direction of the female connection portions. However, the first connector surface may also be rounded or slanted towards the surrounding guiding edge, and may e.g. have an inwardly concave shape.

It is further preferred that the male connecting portions have an axial extension such that they are brought into contact with the first connector surface prior to engagement between the engagement/disengagement member and the locking element. This will facilitate the above-discussed guided coupling procedure even further.

To the same end, it is also preferred that the engagement/disengagement member is secured to one of the connector parts in a fixed position relative to a longitudinal axis of said connector part, while being rotatably moveable about said connector part at said fixed position.

Also, it is preferred that the engagement/disengagement member is provided with at least one handle arranged on an external surface thereof.

According to one example embodiment of the invention, the coupling device comprises an end position fixation arrangement providing a snap lock engagement in an engaged end position between the first and second connector parts. For example, a protrusion may be formed in the engagement/disengagement member, and a corresponding recession may be formed in an abutting surface of the other connector part.

A further advantage with this embodiment is that, by providing an end position fixation arrangement with a snap lock engagement that is arranged to snap lock in an end position of the engagement of the coupling device, the user may, regardless of the level of proficiency, receive a clear indication that the coupling device has reached its final position. The snap lock arrangement may comprise a recess and a corresponding protrusion arranged in the engagement/disengagement member or in either the first or the second connector part, respectively, such that when rotatably engaging the coupling device the protrusion enters the recess in the end position. This will efficiently hinder further rotation. Furthermore, the end position fixation arrangement may provide a sound when the end position fastener has reached its end position. The sound may for example be the snap that follows when in the snap lock engagement the protrusion enters the recess when the end position is reached.

According to one example embodiment of the invention, each of the locking element and the engagement/disengagement member may comprise threads arranged to engage with each other. Additionally or alternatively, the engagement/disengagement member may be provided with internal threads, and the locking element be provided with a radially outwardly protruding engagement structure corresponding to said internal threads.

The locking element may be arranged on either the first connector part or the second connector part. The locking element may be arranged with external threads, or a similar protruding structure, and the engagement/disengagement member may be arranged with internal threads. However, the reverse may also be conceivable, where the locking element is arranged with internal threads and the engagement/disengagement member is arranged with external threads. At least one of the external threads or the internal threads may be continuous along a helical thread structure, to ensure that the external and internal threads engage with each other. The threads may be provided in a radial direction of the coupling device.

However, the engagement/disengagement member may engage with the locking element in other ways as well, such as by means of a bayonet coupling, a friction coupling, or the like.

According to one example embodiment of the invention, a final position of the connector parts is reachable by less than 360 degrees rotation between the engagement/disengagement member and the locking element, and preferably less than 180 degrees rotation, and most preferably less than 90 degrees rotation.

In order to provide an easy to use coupling device, the coupling device is, when rotatably engaged with the locking element, arranged to lock the coupling device such that the final position of the engagement/disengagement member is reached by a few turns of the engagement/disengagement member, preferably through less than one turn of the engagement/disengagement member. The number of turns of the engagement/disengagement member, before it reaches its final position, may be adjusted by the angle and location of the threads, the length dimensions, etc.

Further, the angle of the threads is preferably such that locking element will automatically rotate down on the engagement/disengagement member when the first and second connector parts are brought together with low or moderate force. Hereby, mere bringing together of the connector parts will result in the locking element being at least partly rotated into the locked position. This greatly facilitates the coupling procedure, in particular for users having reduced dexterity, since it may e.g. be accomplished by gripping the tubes or the like fixed to the connector part, rather than the connector parts themselves.

According to one example embodiment of the invention, the female connecting portions and the male connecting portions may be arranged with through-holes.

The at least two female connecting portions and the at least two male connecting portions may be arranged with through-holes, such that liquids may be transported in and out through the coupling device. For example, the through-holes may be used to insert a balloon for anal irrigation, or to provide a stent into the tubular arrangement.

According to one example embodiment of the invention, the at least two female connecting portions have each an opening diameter, the opening diameter being different for the at least two female connecting portions.

The size of the diameter of the female connecting portions is determined based on the purpose of use. The size of the diameter may be determined based on the type of tubular arrangement to be used and on what type of material or liquid that is arranged to be transported or inserted. By providing the connecting portions with different diameters, it is ensured that the coupling device always connects the two or more lumens correctly to each other, since each male connecting portion will only match one of the female connecting portions.

The male connecting portions are preferably male luer lock connecting portions, and the female connecting portions are preferably female luer lock connecting portions.

According to a second aspect of the invention, there is provided a method for coupling together parts of a tubular arrangement comprising a coupling arrangement of the above-discussed configuration, wherein the method comprises the steps of:

bringing the at least two male connecting portions of the second connector part in connection with a first connector surface of the first connector part such that the at least two male connecting portions is surrounded with the guiding edge protruding from the first connector surface around the at least two female connecting portions, rotating the second connector part along the first connector surface, while the second connector part is laterally restricted by the guiding edge, engaging the male connection portion of the second connector part with the female connecting portion of the first connector part, and rotating the engagement/disengagement member in relation to the locking element to engage the connection parts together.

The method for engaging a coupling device for tubular arrangements for medical use comprises the same or similar advantages as the first aspect discussed above. The method may also include a step of locking the first connector part and the second connector part together with the help of the engagement/disengagement member.

According to one example embodiment of the invention, the guiding edge of the first connector may be arranged to assist in the step of engaging the male connecting portion of the second connector with the female connecting portion.

According to one example embodiment of the invention, in the step of rotating the engagement/disengagement member, the connector means may reach a final rotation position in less than one turn of the engagement/disengagement member.

According to one example embodiment of the invention, in the step of rotating the engagement/disengagement member, the engagement/disengagement member may reach a final rotation position in less than a half turn of the engagement/disengagement member.

These and other advantages of the current invention will be evident from the following detailed description of specific embodiments.

DETAILED DESCRIPTION OF THE DRAWINGS

These and other aspects of the present invention will now be described in more detail, with reference to the appended drawings showing example embodiments, wherein.

DETAILED DESCRIPTION

The invention will be described in the following for exemplifying purposes by way of embodiments and with reference to the accompanying drawings.

In the following, with reference to FIG. 1-FIG. 5, different aspects of the invention are illustrated.

Figure 1:
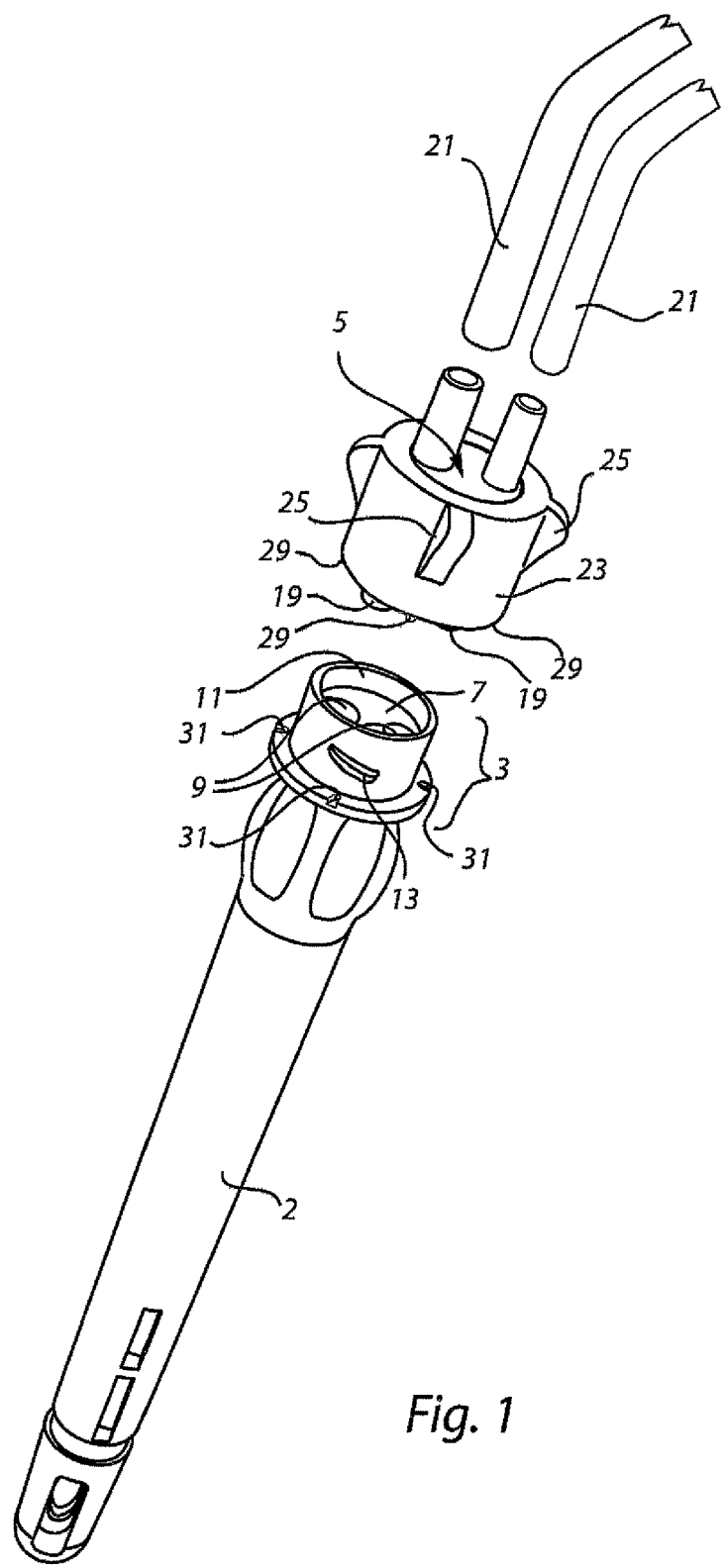
FIG. 1 is an exploded perspective view from above of an embodiment of a coupling device in accordance with one embodiment of the present invention.

In FIG. 1 a coupling device 1 is illustrated, which is separated in a first connector part 3 and a second connector part 5. The first connector part 3 is fixedly connected to a tubular arrangement 2 for medical use, in this case a catheter. The first connector part 3 have a first connector surface 7 arranged with two female connecting portions 9. The two female connecting portions 9 are surrounded by a guiding edge 11 arranged to facilitate the engagement of the coupling device 1, even for the persons with reduced dexterity. In FIG. 1, a locking device 13 is arranged on the outer surface of the guiding edge 11. Furthermore, the locking device 13 here comprises external threads.

Figure 2:
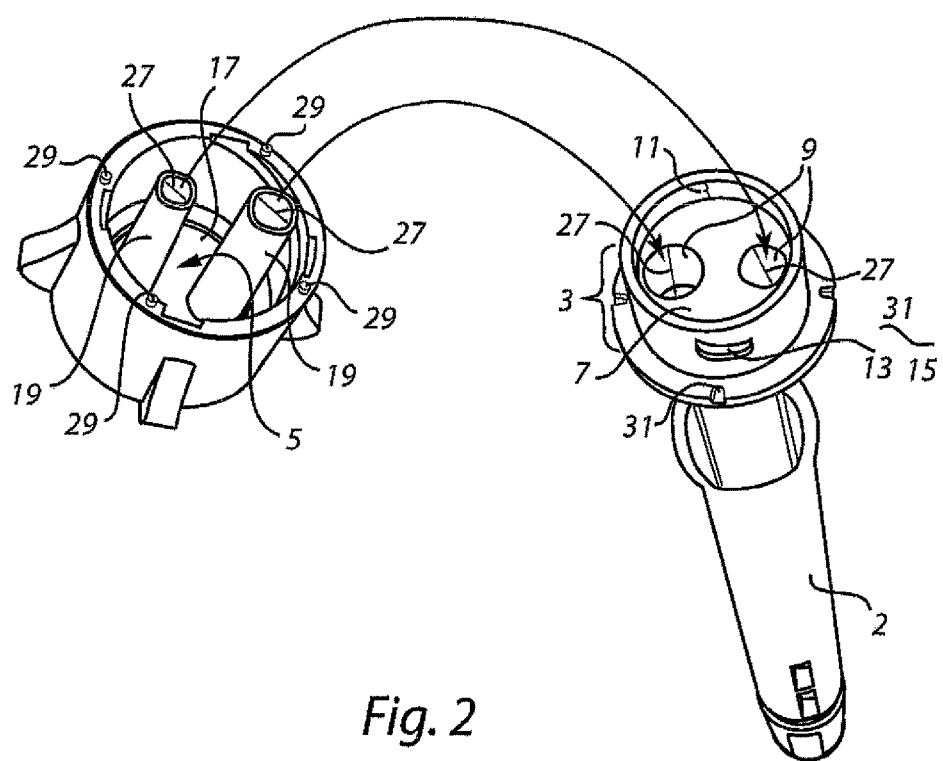
FIG. 2 is another exploded perspective view from above of the embodiment shown in FIG. 1.

The second connector part 5 comprises two male connecting portions 19 protruding orthogonally from a second connector surface (not shown). In FIG. 2, the two male connecting portions 19 are also protruding in the opposite side of the second connector surface, such that each of the two male connecting portions 19 may be connected with a tube 21 for transporting for example irrigation fluid. The second connector part 5 is rotatably connected to an engagement/disengagement member 23. The engagement/disengagement member 23 is here in the form of a locking cuff arranged to engage with the locking device 13 on the first connector part 3, such that the coupling device 1 may be locked. When locking the coupling device 1, the first connector part 3 and the second connector part 5 locked together through rotation. The outer surface of the engagement/disengagement member 23 is, in FIG. 1, arranged with handles 25 protruding radially to facilitate rotation.

Figure 4:
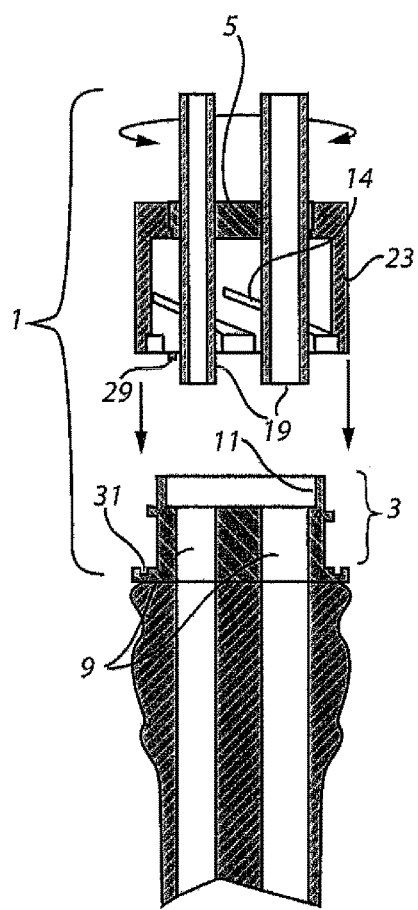
FIG. 4 is an exploded cross-sectional side view of the connector parts of the embodiment shown in FIGS. 1-2 in a non-coupled position.

The engagement/disengagement member may be loose in relation to the connector part, and only fixated during engagement with the other connector part. However, preferably the engagement/disengagement member 23 is secured to the connector parts in a fixed position relative to a longitudinal axis of the connector part, while being rotatably moveable about said connector part at said fixed position. This may, as best seen in FIG. 4, be obtained by providing a circular disk on the connector part, and providing a recess for receiving the edges of this disk in the engagement/disengagement member.

The disk is further preferably arranged at an upper part of the engagement/disengagement member—i.e. opposite to the interface towards the other connector part. Hereby, a relatively smooth and planar upper surface is obtained, which is easy to maintain clean and tidy.

Furthermore, FIG. 2 illustrates the coupling device 1 as described above in reference to FIG. 1 in a disengaged state, with arrows illustrating how the male connecting portions 19 are to be coupled to the female connecting portions 9. The first connector part 3 is fixedly connected to a catheter 2. In FIG. 2, the second connector part 5 displays the second connector surface 17 that was not shown in FIG. 1. The two male connecting portions 19 are, in FIG. 2, protruding substantially parallel to a rotation axis of the second connector part 5. The two male connecting portions 19 and the female connecting portions 9 are both arranged with through-holes such that any one of fluid, medical material, human tissue and/or blood may be transported in and/or out of the through-holes. Furthermore, the fluid may for example be irrigation fluid and the medical material may be a stent, a catheter for anal irrigation or the like.

In FIG. 2, the opening diameters 27 of the two male connecting portions are different from each other. However, it may also be conceivable that the male connecting portions have the same opening diameters 27. The two female connecting portions 9 may protrude substantially orthogonally from a flat first connector surface 7 with different opening diameters 27. However, for some embodiment it may be conceivable that each of the at least two female connecting portions 9 have the same opening diameter 27. Both the female connecting portions 9 and the male connecting portions 19 may alter their diameter in an axial direction. Possible shapes for the female and the male connecting portions may, for example, be cone-shaped, cylinder-shaped or cup-shaped. The male and the female connecting portions may preferably be arranged to have a diameter, which is decreasing further away from the second connector surface and the first connector surface, respectively, to further facilitate the engagement of the coupling device 1. Most preferably, the male and female connection portions together form a luer lock connection.

The first connector part 3 have a locking element 13 arranged on the outer side of the guiding edge 11. The locking element 13 is an external thread arranged to engage in the corresponding internal thread 14 in the engagement/disengagement member 23. As is illustrated in FIG. 2 the external thread 15, which is protruding, does not extend as far in the radial direction as the internal thread in the helical thread structure. One of the internal threads 14 or the external threads 15 may provide a complete uninterrupted helical thread structure while the other may provide a thread that is interrupted and does not extend as far as the other in the radial direction. Even though the external thread 15 does not provide an uninterrupted helical thread structure, the internal thread provides a complete helical structure on the inside of the engagement/disengagement member beginning at a rim of the engagement/disengagement member 23 such that external thread is easily guided to an end position of the engagement/disengagement member 23. The end position of the engagement/disengagement member 23 is reached when the first connector part 3 and the second connector part 5 are locked together. The internal thread 29 may begin at the rim of the engagement/disengagement member 23.

Figure 3:
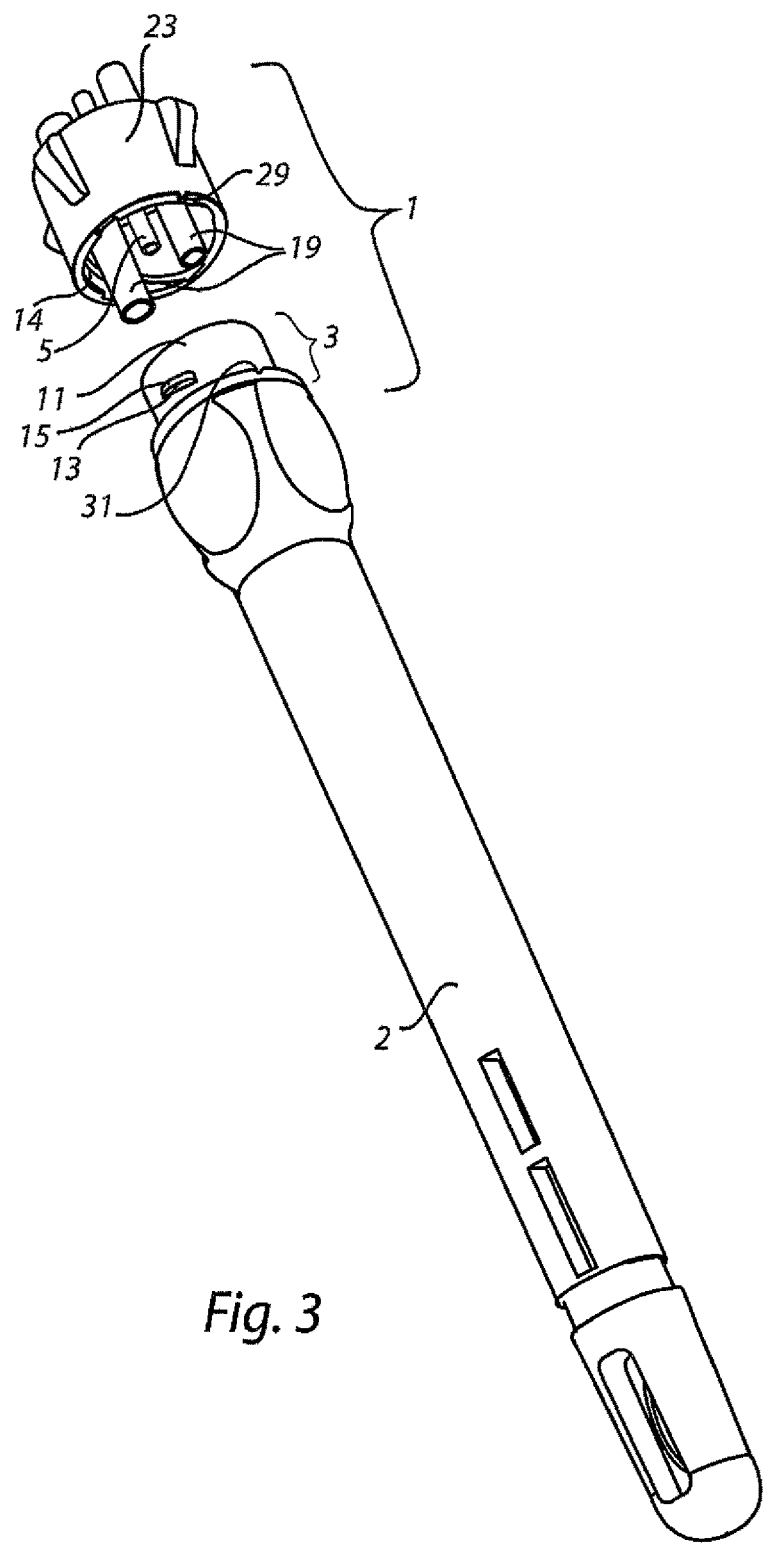
FIG. 3 is an exploded perspective view from below of another embodiment of a coupling device in accordance with the present invention.

In FIG. 3, another embodiment of the coupling device is illustrated. This coupling device is generally similar to the coupling device 1 as described above in reference with both FIG. 1 and FIG. 2. However, the coupling device 1 is here provided with three male connecting portions 19 arranged to transport different fluid and material in and/or out of the body. Correspondingly, FIG. 3 has three female connecting portions 9 (not shown) in the first connector part 3 adapted to receive the three male connecting portions 19. The coupling device is arranged to have at least two or more male 19 and correspondingly sized female connecting portions 9. The male connecting portions 19 and corresponding female connecting portions 9 may be used for additional transportation.

Furthermore, the coupling device 1 comprises an end position fastener or fixation arrangement that provides a snap lock arrangement. The snap lock arrangement is arranged on a rim of the engagement/disengagement member facing the first connector part 3 and on the first connector part 3. In the engagement/disengagement member, a ridge 29 is protruding, arranged to engage with a corresponding recess 31 arranged in the first connector part 3. When the end position fastener reaches its end position, the ridge 29 of the engagement/disengagement member engages with the recess 31 of the first connector part 3 such that the coupling device is locked. Furthermore, the engagement of the recess 31 and the ridge 29 may further provide a snap sound, which indicates to the user that the coupling device has been properly engaged. Furthermore, the recess 31 may be arranged in the engagement/disengagement member 23 and the ridge 29 may be arranged in the first connector part 3.

Naturally, such a fastener/fixation arrangement may also be provided in the above-discussed first embodiment.

In FIG. 4, a first step towards engaging the coupling device is illustrated by a cross-section of the first connector part 3 and the second connector part 5. The two male connecting portions 19 are protruding from the second connector surface 17 in the second connector part 5 facing the first connector part 3. The two male connecting portions 19 are arranged to be brought in contact with the first connector surface 7 of the first connector part 3, such that the guiding edge 11 surrounds the two male connecting portions 19 keeping them from lateral movements. The second connector part 5 is kept in a position by the guiding edge 11, such that the two male connecting portions 19 engages with the correspondingly sized two female connections portions 9 when rotating less than one turn of the second connector part 5. Furthermore, it is also conceivable that the rotation arranged to engage the male and female connecting portions is performed by the first connector part 3. The engagement/disengagement member may also be rotated along with the first connector part 3 or the second connector part 5. The engagement of the coupling device 1 becomes much easier with the guiding edge 11, since it reduces the need for precision. It is much easier to bring the two male connecting portions to the first connector part 3 such that they are surrounded by the guiding edge 11, than to fit them directly into the female connecting portions. By directly engaging the two male connecting portions 19 in corresponding female connecting portions 9 there will be an increased demand on precision since the opening of the female connecting portions 9 is smaller than the surface that is surrounded by the guiding edge 11. Furthermore, the angle of the second connector part 5 must also be arranged in a proper position to be able to engage the male connecting portions 19 with the female connecting portions 9. However, by using a guiding edge 11, it is not necessary to have the same level of precision when engaging the coupling device and it is unnecessary to take into account the angle of the first 3 and second connector part 5.

Figure 5:
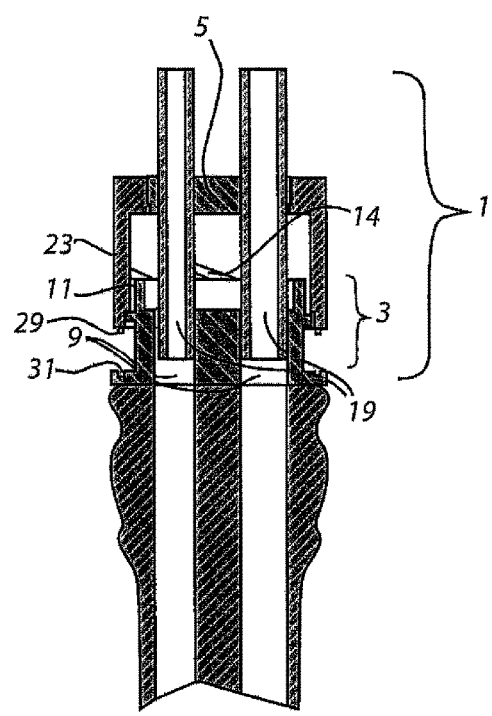
FIG. 5 is a cross-sectional side view of the connector parts of the embodiment shown in FIGS. 1-2 in a coupled position.

FIG. 5 is a cross-sectional side view of the two male connecting portions 19 of the second connector part 5 engaged with the two female connecting portions 9 of the first connector part 3. FIG. 5 illustrates the step after FIG. 4, when after rotating one of the first and the second connector part, the male connecting portions and the female connecting portions have engaged with each other. When the at least two male connecting portions 19 have engaged with the female connecting portions 9, the engaging/disengaging member 23 is further rotated such that it the internal thread 14 engages with the locking element 13 of the first connector part 3, and locks the first connector part 3 and the second connector part 5 together.

The invention has been described above by ways of embodiments. Several variants of the invention are, however, conceivable. For example, it is possible for the first connector surface 17 and the guiding edge 11 to form a recess in the shape of a cone, cup, or any other circular symmetric recess. Furthermore, the first connector surface 17 may also have a circular symmetric undulation pattern. Additionally, it is possible to provide an engagement/disengagement member 23 that is rotatably connected to the first connector part 3. The locking element 13 and the internal threads 29 may instead of providing a threaded engagement provide a bayonet coupling, a friction coupling or any other type of coupling for locking the first connector part 3 and the second connector part 5 together with the help of the engagement/disengagement member. In the illustrated cases, the first connector part 3 has been fixedly connected to a catheter. However, it is also conceivable for the catheter 2 to be fixedly connected to the second connector part 5.

Furthermore, the guiding edge 11 may not be a continuous edge. However, the gaps in the guiding edge 11 is preferably smaller than the smallest diameter of the male connecting portions 19 to ensure that the second connector part 5 is easily guided by the guiding edge 11.

Additionally, the guiding edge 11 may further, in some embodiments, be shaped as an evenly cornered polygon, with at least 6 corners.

The coupling device 1 may, for example, be made out of any a plastic material, but other materials, such as metal may also be considered for at least part of the coupling device.

Such obvious variants must be considered to be comprised by the invention as defined by the appended claims.

The invention claimed is:

1. A coupling device for a tubular arrangement for medical use comprising:
a first connector part; and
a second connector part;
wherein one of said connector parts comprises an engagement/disengagement member for at least assisting in engaging and disengaging the engagement between said connector parts;
wherein the other of said connector parts comprises a locking element arranged to rotatably engage with the engagement/disengagement member;
wherein the first connector part comprises at least two female connecting portions arranged in a first connector surface;
wherein the second connector part comprises at least two corresponding male connecting portions arranged in a second connector surface, and
wherein the first connector part further comprises a non-movable guiding edge protruding from the first connector surface towards the second connector part, the guiding edge forming a circumferential surface that fixedly surrounds said at least two female connecting portions such that the guiding edge and the first connector surface together form a recessed surface to allow insertion of the at least two male connecting portions into the recessed surface, whereby the guiding edge enables rotation of the at least two male connection portions along the first connector surface when inserted into the recessed surface until they engage with the at least two female connecting portions.

2. The coupling device according to claim 1, wherein the tubular arrangement is a catheter and at least one of the first and the second connector part is fixedly connected to said catheter.

3. The coupling device according to claim 1, wherein the guiding edge has a circular shape arranged to surround the at least two female connecting portions of the first connector part.

4. The coupling device according to claim 1, further comprising an end position fixation arrangement providing a snap lock engagement in an engaged end position between the first and second connector parts.

5. The coupling device according to claim 1, wherein each of the locking element and the engagement/disengagement member comprise threads arranged to engage with each other.

6. The coupling device according to claim 1, wherein a final engaged position of the connector parts is reachable by less than 360 degrees rotation between the engagement/disengagement member and the locking element.

7. The coupling device according to claim 1, wherein the female connecting portions and the male connecting portions are arranged with through-holes.

8. The coupling device according to claim 1, wherein the at least two female connecting portions each have an opening diameter, the opening diameters being different for the at least two female connecting portions.

9. The coupling device according to claim 1, wherein the engagement/disengagement member is secured to one of the connector parts in a fixed position relative to a longitudinal axis of said connector part, while being rotatably moveable about said connector part at said fixed position.

10. The coupling device according to claim 1, wherein the first connector surface is essentially planar, and arranged essentially perpendicular to the axial direction of the female connection portions.

11. The coupling device according to claim 1, wherein the engagement/disengagement member is provided with internal threads, and wherein the locking element is provided with a radially outwardly protruding engagement structure corresponding to said internal threads.

12. The coupling device according to claim 1, wherein the male connecting portions have an axial extension such that they are brought into contact with the first connector surface prior to engagement between the engagement/disengagement member and the locking element.

13. The coupling device according to claim 1, wherein the engagement/disengagement member is provided with at least one handle arranged on an external surface thereof.

14. The coupling device according to claim 1, wherein the male connecting portions are male luer lock connecting portions, and wherein the female connecting portions are female luer lock connecting portions.

15. The coupling device according to claim 1, wherein the tubular arrangement is a catheter for anal irrigation and at least one of the first and the second connector part is fixedly connected to said catheter.

16. The coupling device according to claim 1, wherein a final engaged position of the connector parts is reachable by less than 180 degrees rotation between the engagement/disengagement member and the locking element.

17. The coupling device according to claim 1, wherein a final engaged position of the connector parts is reachable by less than 90 degrees rotation between the engagement/disengagement member and the locking element.

18. The coupling device of claim 1, wherein the locking element is arranged on an outer surface of the guiding edge.

19. The coupling device of claim 18, wherein the locking element comprises external threads.

20. A method for coupling together parts of a tubular arrangement comprising a coupling arrangement in accordance with claim 1, wherein the method comprises the steps of:
- bringing the at least two male connecting portions of the second connector part in connection with a first connector surface of the first connector part such that the at least two male connecting portions is surrounded with the guiding edge protruding from the first connector surface around the at least two female connecting portions;
- rotating the second connector part along the first connector surface, while the second connector part is laterally restricted by the guiding edge;
- engaging the male connection portion of the second connector part with the female connecting portion of the first connector part; and
- rotating the engagement/disengagement member in relation to the locking element to engage the connection parts together.

* * * * *